United States Patent
Schütz

[11] Patent Number: 6,089,862
[45] Date of Patent: Jul. 18, 2000

[54] TENSIONING SCREW FOR ORTHODONTIC ADJUSTMENT DEVICES

[76] Inventor: Winfried Schütz, Wilhelm-Hoegner-Str. 58, D-81737 Munich, Germany

[21] Appl. No.: 09/338,294

[22] Filed: Jun. 23, 1999

[51] Int. Cl.$^7$ .................................................. A61C 3/00
[52] U.S. Cl. ............................... 433/18; 433/19; 433/7
[58] Field of Search ............................. 435/7, 18, 19, 435/22, 24, 173

[56] References Cited

U.S. PATENT DOCUMENTS 4,483,674  11/1984  Schuetz ................................. 433/22
4,571,178  2/1986  Rosenberg ............................. 433/7
4,723,910  2/1988  Keller .................................... 433/7
5,482,463  1/1996  Wilson, Jr. et al. ................. 433/173
5,873,715  2/1999  Liou ................................... 433/7 X

*Primary Examiner*—Nicholas D. Lucchesi
*Attorney, Agent, or Firm*—Milde, Hoffberg & Macklin, LLP

[57] ABSTRACT

A tensioning screw for orthodontic teeth straightening devices employed to adjust the situation and position of teeth along the curve of the jaw. The screw includes a nut and a threaded shaft that extends through it. An essentially resilient component (11) is disposed between the nut (6) and the shaft (2), at least on one side where the shaft enters or leaves the nut, and rests against the shaft's threads to prevent the shaft from undesired turning with respect to the nut.

11 Claims, 2 Drawing Sheets

TENSIONING SCREW FOR ORTHODONTIC ADJUSTMENT DEVICES

BACKGROUND OF THE INVENTION

The present invention concerns a tensioning screw for orthodontic teeth straightening devices.

Tensioning screws of this type are known from the present applicant's U.S. Pat. No. 4,483,674. They are employed to adjust the situation and position of teeth or groups of teeth along the curve of the jaw. They include a nut and a threaded shaft that extends through it, tensioned between two points within the device. The effective length of the shaft is shortened during treatment to adjust the situation and position of the teeth.

Such screws have proved effective in practice for this purpose. Still, the shaft will sometimes automatically turn backward, or even slowly out of the nut, due for example to the wearer's chewing motions. Attempts have been made to prevent this by using self-locking threads, but they are complicated to manufacture and make the screws more expensive. It also becomes almost impossible to screw the screw backwards when necessary, and, when one has been screwed in too tight, it must usually be discarded.

SUMMARY OF THE INVENTION

The object of the present invention is to provide a tensioning screw of the aforesaid type that will reliably prevent the shaft from turning backward out of the nut but that can be partly unscrewed and secured in that position without loss of function.

This object, as well as other objects which will become apparent from the discussion that follows, are achieved, in accordance with the present invention, by providing an essentially resilient component squeezed between the nut and the shaft, resting against the shaft's threads, and generating there a tension essentially perpendicular to the length of the shaft.

The resilient component can preferably be a ring or double loop in the shape of a figure eight resting against or enclosing the shaft on each side of the nut where the shaft enters or leaves it.

The nut in one embodiment of the present invention has a projection on each side where the shaft enters or leaves it. The resilient ring or figure eight is introduced between the projections. The ring will accordingly be slightly squeezed and will press against the threads on the shaft, reliably securing them in position and preventing automatic backward rotation.

The projections on each side of the nut can be in the form of pins, of strong wire perhaps, that secure the screw in the aforesaid orthodontic adjustment device.

The resilient component in one very simple embodiment is in the shape of a figure eight, the two loops attached to each other along a web. The figure eight is positioned with the web more or less between, and extending along the circumference of each loop, each of which extends around the shaft. In this version, the web will rest against one side of the shaft and the loops against the other side. This embodiment requires no projections or pins extending out of the nut to secure the resilient component, although it may of course have one. It is in particular possible to secure to the nut at least one sleeve essentially paralleling the shaft and sliding along an arc of wire on the orthodontic adjustment device. The screw can accordingly be secured not only to clamps mounted on the teeth but also directly to the arc extending through the clamps.

For a full understanding of the present invention, reference should now be made to the following detailed description of the preferred embodiments of the invention as illustrated in the accompanying drawings.

DESCRIPTION OF THE PREFERRED EMBODIMENTS

Figure 1:
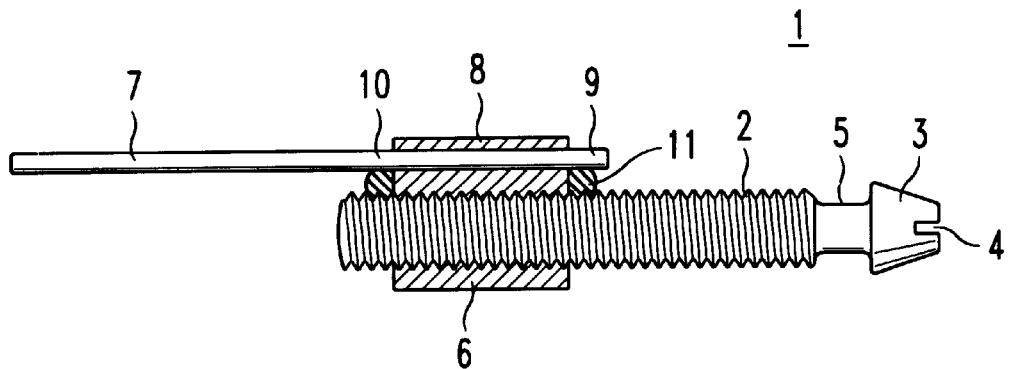
FIG. 1 is a partly sectional side view of a tensioning screw in accordance with the present invention with a resilient ring as a brake for the threaded shaft.

The preferred embodiments of the present invention will now be described with reference to FIGS. 1–5 of the drawings. Identical elements in the various figures are designated with the same reference numerals.

The tensioning screw 1 illustrated in FIG. 1 has an outside-threaded shaft 2 with a head 3 provided with a slot 4 for a screwdriver. Between head 3 and the threaded section is a slender neck 5 that can accommodate an unillustrated ligature wire as a fastening to one point on an orthodontic adjustment device. Shaft 2 engages and inside-threaded nut 6. Fastened to nut 6 and paralleling shaft 2 is a pin 7. As will be evident from the figure, pin 7 is inserted in a sleeve 8 and secured by laser or spot welding for example. Pin 7 could alternatively be secured directly to the circumference of the nut, by laser welding for example. The end of pin 7 that points toward head 3 extends slightly beyond nut 6, constituting a projection 9. The other end of pin 7 extends considerably—as far, perhaps, as the shaft 2 is long—beyond nut 6, and can be inserted into the auxiliary tube of a molar band. The screw will accordingly also be attached to the band. The section of pin 7 on the side of nut 6 remote from projection 9 can be considered another projection 10 extending beyond the nut.

Figure 2:
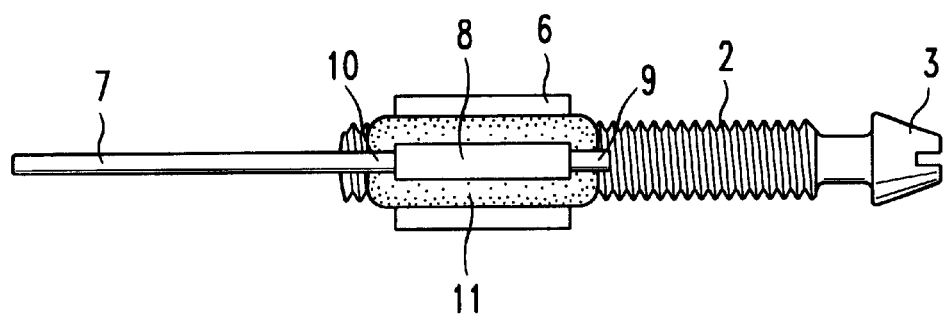
FIG. 2 is a top view of the screw in FIG. 1.
Figure 3:
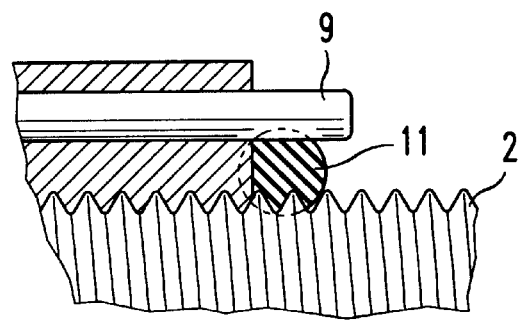
FIG. 3 is a detail of FIG. 1, illustrating how the ring works.

A resilient ring 11 is now inserted tightly into the screw as illustrated in FIG. 2 between projections 9 and 10 and the threads on shaft 2. Ring 11 extends between the projections on each side of pin 7 or sleeve 8. The hatched area in FIG. 3 represents the deformation in ring 11 once it has been inserted, the broken line indicating its original shape. The deformation of ring 11 forces it against the threads on shaft 2 and prevents the shaft from turning backward.

Figure 4:
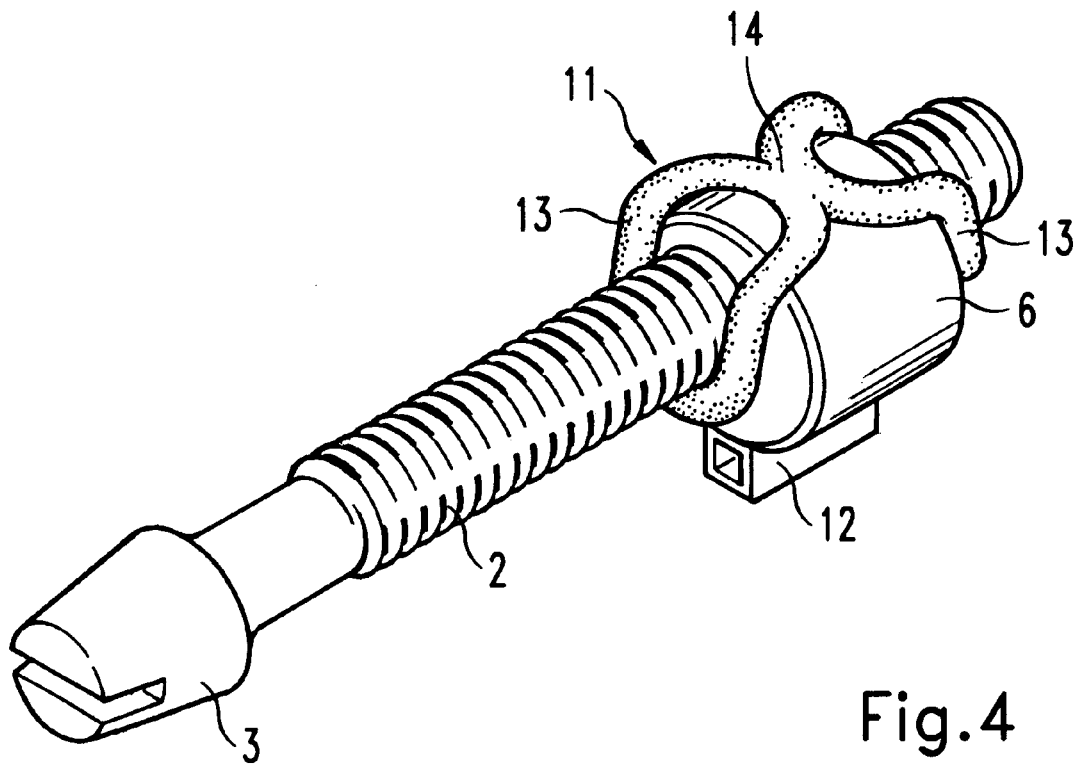
FIG. 4 is a perspective view of another embodiment of a tensioning screw in accordance with the present invention.

FIG. 4 illustrates another embodiment of a screw 1 in accordance with the present invention, also with a shaft 2 with a head 3 and a nut 6. Nut 6 is provided with a sleeve 12 essentially paralleling shaft 2. Sleeve 12 can be slipped onto the wire arc of an orthodontic adjustment device that extends through clamps mounted on the teeth.

Figure 5:
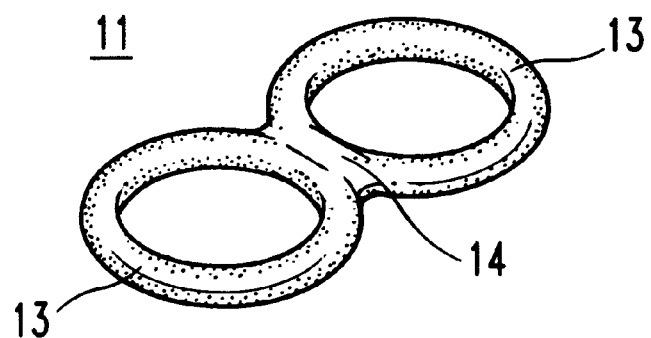
FIG. 5 illustrates a resilient ring intended for the screw illustrated in FIG. 4.

The nut 6 in this embodiment has no projections on the side facing sleeve 12. It employs instead a different kind of resilient component essentially in the form of a figure eight 11 as illustrated in FIG. 5. Figure eight 11 has two loops 13 connected along a web 14 between them and extending along the circumference of each loop. Each loop 13 wraps around shaft 2 on opposite sides of nut 6 and accordingly rests snugly against the shaft's threads, preventing it from turning backward. As in the previous embodiment, however, it is till possible to turn shaft 2 in either direction in the threads inside nut 6.

There has thus been shown and described a novel tensioning screw for orthodontic adjustment devices which fulfills all the objects and advantages sought therefor. Many changes, modifications, variations and other uses and applications of the subject invention will, however, become apparent to those skilled in the art after considering this specification and the accompanying drawings which disclose the preferred embodiments thereof. All such changes, modifications, variations and other uses and applications which do not depart from the spirit and scope of the invention are deemed to be covered by the invention, which is to be limited only by the claims which follow.

What is claimed is:

1. In a tensioning screw for orthodontic teeth straightening devices employed to adjust the situation and position of teeth along the curve of the jaw, including a nut and a threaded shaft that extends through it, the improvement comprising an essentially resilient component disposed between the nut and the shaft at least on one side where the shaft enters or leaves the nut and resting against the shaft's threads, to prevent undesired rotation of the shaft with respect to the nut, wherein the essentially resilient component rests against the shaft's threads on both sides where the shaft enters and leaves the nut.

2. The tensioning screw defined in claim 1, wherein the resilient component is a ring.

3. The tensioning screw defined in claim 1, further comprising at least one sleeve secured to the nut, essentially paralleling the shaft, and sliding along an arc of wire on the orthodontic adjustment device.

4. In a tensioning screw for orthodontic teeth straightening devices employed to adjust the situation and position of teeth along the curve of the jaw, including a nut and a threaded shaft that extends through it, the improvement comprising an essentially resilient component disposed between the nut and the shaft at least on one side where the shaft enters or leaves the nut and resting against the shaft's threads, to prevent undesired rotation of the shaft with respect to the nut, wherein the nut has a projection on each side where the shaft enters or leaves it and wherein the resilient component is introduced between these projections, the component being slightly squeezed and pressing against the threads on the shaft, reliably securing them in position and preventing undesired backward rotation of the shaft.

5. The tensioning screw defined in claim 4, wherein the projections on each side of the nut are in the form of pins that secure the screw to the orthodontic straightening device.

6. The tensioning screw defined in claim 4, wherein the resilient component is a ring.

7. The tensioning screw defined in claim 4, further comprising at least one sleeve secured to the nut, essentially paralleling the shaft, and sliding along an arc of wire on the orthodontic adjustment device.

8. In a tensioning screw for orthodontic teeth straightening devices employed to adjust the situation and position of teeth along the curve of the jaw, including a nut and a threaded shaft that extends through it, the improvement comprising an essentially resilient component disposed between the nut and the shaft at least on one side where the shaft enters or leaves the nut and resting against the shaft's threads, to prevent undesired rotation of the shaft with respect to the nut, wherein the resilient component is essentially in the shape of a figure eight with two loops joined together along a web.

9. The tensioning screw defined in claim 8, wherein the web rests against the nut, each loop extending around the shaft.

10. The tensioning screw defined in claim 8, wherein the resilient component is a ring.

11. The tensioning screw defined in claim 8, further comprising at least one sleeve secured to the nut, essentially paralleling the shaft, and sliding along an arc of wire on the orthodontic adjustment device.

\* \* \* \* \*